(12) United States Patent
Rylander et al.

(10) Patent No.: US 11,058,291 B2
(45) Date of Patent: Jul. 13, 2021

(54) DEVICES, SYSTEMS AND METHODS FOR CLEANING OF ELONGATED INSTRUMENT SURFACE

(71) Applicants: BOARD OF REGENTS, THE UNIVERSITY OF TEXAS SYSTEM, Austin, TX (US); ASCENSION TEXAS, Austin, TX (US)

(72) Inventors: Christopher Rylander, Austin, TX (US); Christopher Idelson, Austin, TX (US); John Uecker, Austin, TX (US)

(73) Assignees: BOARD OF REGENTS, THE UNIVERSITY OF TEXAS SYSTEM, Austin, TX (US); ASCENSION TEXAS, Austin, TX (US)

( * ) Notice: Subject to any disclaimer, the term of this patent is extended or adjusted under 35 U.S.C. 154(b) by 0 days.

(21) Appl. No.: 16/939,448

(22) Filed: Jul. 27, 2020

(65) Prior Publication Data

US 2020/0397272 A1 Dec. 24, 2020

Related U.S. Application Data

(63) Continuation of application No. PCT/US2019/063369, filed on Nov. 26, 2019.
(Continued)

(51) Int. Cl.
*A61B 1/12* (2006.01)
*A61B 1/00* (2006.01)
(Continued)

(52) U.S. Cl.
CPC .......... *A61B 1/126* (2013.01); *A61B 1/00135* (2013.01); *A61B 1/3132* (2013.01);
(Continued)

(58) Field of Classification Search
CPC ......... A61B 1/00; A61B 1/12; A61B 1/00087; A61B 1/00135; A61B 1/00142;
(Continued)

(56) References Cited

U.S. PATENT DOCUMENTS 5,392,766 A 2/1995 Masterson et al.
5,518,502 A 5/1996 Kaplan et al.
(Continued)

FOREIGN PATENT DOCUMENTS

CA 2400381 8/2001
CN 202136313 U 2/2012
(Continued)

OTHER PUBLICATIONS

International Search Report and Written Opinion issued in International Application No. PCT/US2019/063369, dated Feb. 12, 2020.
(Continued)

*Primary Examiner* — Ryan N Henderson
(74) *Attorney, Agent, or Firm* — Parker Highlander PLLC

(57) ABSTRACT

Devices, systems and methods for cleaning a surface of as elongated instrument held within a cavity. In particular embodiments of the device, a longitudinal wire member extends along an elongated instrument (e.g. a laparoscope) and a rotatable transverse member removes matter from a surface of the instrument (e.g. a lens).

9 Claims, 9 Drawing Sheets

Related U.S. Application Data

(60) Provisional application No. 62/773,060, filed on Nov. 29, 2018.

(51) Int. Cl.
*A61B 90/70* (2016.01)
*A61B 1/313* (2006.01)

(52) U.S. Cl.
CPC .......... *A61B 90/70* (2016.02); *A61B 1/00096* (2013.01); *A61B 1/127* (2013.01); *A61B 2090/701* (2016.02)

(58) Field of Classification Search
CPC ......... A61B 1/126; A61B 1/127; A61B 90/70; A61B 2090/701; A61B 1/00096; A61B 1/3132
See application file for complete search history.

(56) References Cited

U.S. PATENT DOCUMENTS

| | | | |
|---|---|---|---|
| 5,658,273 A | 8/1997 | Long | |
| 6,354,992 B1 | 3/2002 | Kato | |
| 6,755,782 B2 | 6/2004 | Ogawa | |
| 6,905,078 B1* | 6/2005 | Gattuso | B05B 3/0413 239/11 |
| 6,923,759 B2 | 8/2005 | Kasahara et al. | |
| 7,543,314 B2 | 6/2009 | Kadykowski | |
| 7,775,970 B2* | 8/2010 | Maeda | A61B 1/00135 600/106 |
| 7,959,561 B2 | 6/2011 | Akui et al. | |
| 8,001,984 B2 | 8/2011 | Sasaki | |
| 3,047,215 A1 | 11/2011 | Sasaki | |
| 8,535,220 B2 | 9/2013 | Mondschein | |
| 8,690,764 B2 | 4/2014 | Clark et al. | |
| 8,979,738 B2 | 3/2015 | Hsu et al. | |
| 9,486,129 B2 | 11/2016 | Rodriguez Sanjuan | |
| 9,632,019 B2* | 4/2017 | Karagoz | G01N 21/15 |
| 9,763,567 B2 | 9/2017 | O'Prey et al. | |
| 9,913,576 B2 | 3/2018 | Ray et al. | |
| 10,201,396 B2 | 2/2019 | Rosenbaum et al. | |
| 2002/0065450 A1 | 5/2002 | Ogawa | |
| 2003/0233723 A1* | 12/2003 | Lizotte | G01N 33/18 15/250.001 |
| 2005/0159764 A1* | 7/2005 | Kasahara | A61B 17/00008 606/159 |
| 2006/0199998 A1* | 9/2006 | Akui | A61B 1/00135 600/127 |
| 2006/0293559 A1 | 12/2006 | Grice et al. | |
| 2008/0306335 A1* | 12/2008 | Lau | A61B 1/018 600/106 |
| 2009/0229067 A1* | 9/2009 | Becker | A61B 1/126 15/250.361 |
| 2009/0240111 A1 | 9/2009 | Kessler et al. | |
| 2009/0250081 A1 | 10/2009 | Gordin et al. | |
| 2010/0139018 A1 | 6/2010 | Maslanka | |
| 2012/0101338 A1 | 4/2012 | O'Prey et al. | |
| 2012/0108904 A1* | 5/2012 | Ma | A61B 1/126 600/175 |
| 2013/0053639 A1 | 2/2013 | Ihde | |
| 2014/0094650 A1 | 4/2014 | Schaning | |
| 2014/0171739 A1 | 6/2014 | Nguyen | |
| 2014/0246051 A1 | 9/2014 | Hurst | |
| 2014/0261545 A1* | 9/2014 | Jenkins | A61B 1/00135 134/8 |
| 2015/0282695 A1* | 10/2015 | Tay | G02B 23/2476 600/124 |
| 2017/0215986 A1 | 8/2017 | Brody et al. | |
| 2017/0311789 A1* | 11/2017 | Mulcahey | A61B 1/00101 |
| 2017/0332893 A1 | 11/2017 | Irion et al. | |
| 2017/0367571 A1 | 12/2017 | Nave | |
| 2018/0110406 A1* | 4/2018 | Sarnaik | A61B 1/00135 |
| 2018/0116496 A1* | 5/2018 | Arcot | A61B 1/00135 |
| 2018/0344141 A1* | 12/2018 | Rosenbaum | A61B 1/00089 |

FOREIGN PATENT DOCUMENTS

| | | | | |
|---|---|---|---|---|
| CN | 102578999 | | 7/2012 | |
| CN | 202892095 | | 4/2013 | |
| CN | 101883531 B | | 7/2014 | |
| CN | 203917219 | | 11/2014 | |
| EP | 0647425 A1 | | 4/1995 | |
| JP | S5861723 A | | 4/1983 | |
| JP | H01204637 A | | 8/1989 | |
| JP | 04-362912 | | 12/1992 | |
| JP | H05103748 A | | 4/1993 | |
| JP | 2005040184 A | * | 2/2005 | ............. A61B 1/126 |
| JP | 2007117103 A | * | 5/2007 | ............. A61B 1/126 |
| JP | 2007117289 A | * | 5/2007 | ......... A61B 1/00087 |
| JP | 2008279202 A | * | 11/2008 | ............. A61B 1/126 |
| JP | 2015031026 A | | 2/2015 | |
| JP | 5735908 B2 | | 6/2015 | |
| KR | 20110130268 A | | 12/2011 | |
| WO | 2009046234 A2 | | 4/2009 | |
| WO | 2009125387 A2 | | 10/2009 | |
| WO | 2014034839 A1 | | 3/2014 | |
| WO | WO2017006684 | | 12/2017 | |
| WO | 2018093817 A1 | | 5/2018 | |

OTHER PUBLICATIONS

Machine translation of JP 2015031026, dated Feb. 1, 2015.

Till, H. R., and N. R. Lindblad. "Parametric study of a xerographic cleaning blade." Conference record annual meeting IEEE industry. 1976.

Harpavat, Ganesh L. "A theoretical study of the mechanics of a xerographic cleaning blade." IEEE Transactions on Industry Applications 6 (1979): 681-687.

\* cited by examiner

DEVICES, SYSTEMS AND METHODS FOR CLEANING OF ELONGATED INSTRUMENT SURFACE

CROSS-REFERENCE TO RELATED APPLICATIONS

This application is a continuation of International Application No. PCT/US2019/063369, filed Nov. 26, 2019, which claims priority to U.S. Provisional Patent Application Ser. No. 62/773,060 filed Nov. 29, 2018, the entire contents of each of which are incorporated herein by reference.

BACKGROUND INFORMATION

In certain instances, it can be desirable to clean a surface of an elongated instrument while the surface is held in a cavity. For example, during laparoscopic surgery the vision through the laparoscope may be impaired. For example, the scope may become fogged, or the scope may be smeared by blood or other bodily fluids or tissues (e.g. interstitial fluid or fat tissue).

Currently, two different scope cleaning methods are commonly utilized. One method is to remove the laparoscope from the body, wipe the lens with a cloth, and reinsert it into the body. This method, though effective, is time consuming and causes the surgeon to lose visual of the surgical site, which can be considered dangerous, as surgical instruments typically remain inside the body.

The action of cleaning the laparoscope increases the length of time each surgical procedure takes, as well as decreases the amount of operating room (OR) time available to the hospital. Additionally, as patients undergo longer procedures, their time spent under anesthesia increases. As increased time under anesthesia has been shown to correlate to a rise in surgical complication rates and post-surgical infection rates, this excess time is not only wasteful, but also potentially medically and financially costly.

The other method is to wipe the laparoscope lens upon a nearby organ or tissue. While the laparoscope remains inside the body and takes less time to clean, this method is not often effective. When using either method, the surgeon must spend time relocating the surgical site within the body. The entire process is a hindrance and an annoyance for surgeons at minimum. Also, it is costly for hospitals, patients, and insurance companies due to wasted time, and possibly surgical complications and post-surgical infections.

Methods comparable to those discussed above (i.e. referring to the field of laparoscopy), are commonly utilized in different fields at the appropriate scale. For example, in down hole drilling applications, instruments that become dirty with debris may need to be removed from the hole and cleaned before resuming use.

There is presently a shortage of methods and devices that provide for effective devices and methods to clean a surface of an elongated instrument held within a cavity. Exemplary embodiments of the present disclosure address these shortcomings.

SUMMARY

Exemplary embodiments of the present disclosure allow for rapid and easy cleaning of an instrument held within a cavity. For example, this may include cleaning a laparoscope in vivo, negating the need for instrument removal from the body.

Embodiments of the present disclosure allow for users of elongated instruments (including for example, laparoscopes or other medical instruments, down hole drilling cameras and equipment, etc.) to clean a surface of the instrument without having to notably remove the instrument from its place of use. For example, in the case of an application for a laparoscope, the present disclosure would allow for the user to clean a surface of a laparoscope (e.g. a lens) in vivo, without having to remove the scope from the body. It therefore significantly decreases the time it takes to clean the instrument surface as compared to current technologies, relieving a vast amount of the technical and financial pains placed on stakeholders. For example, in the case of a laparoscopic application, vast amounts of medical and financial pains may be significantly mitigated by the improvement of an in vivo laparoscope cleaner, thereby benefiting hospitals, clinicians, patients, and third-party payers.

Exemplary methods of cleaning an instrument include mechanical, optical, and pneumatic applications to clear unwanted objects, contaminants, particles, etc. from lens of the instrument. One mechanical embodiment utilizes a proximal member that extends for the length of a laparoscope. This proximal member has a cleaning tip at the distal (lens) end of the laparoscope that allows for cleaning of the laparoscope lens. It also has a base end as well, where the user primarily interacts with the system/device.

This application may use a surface cleaning material at the distal tip to be swept, dragged, rotated, etc. across the lens. The mechanism of this cleaning actuation may be designed to actuate with a passive mechanism that only cleans with relative translation between the scope and proximal member. The mechanism may also be designed to actuate with an active mechanism that cleans when the user implements fine-tuned control of the cleaning tip.

Certain embodiments include a device configured to clean a surface of an elongated instrument, where the device comprises: a longitudinal wire member comprising a proximal end, a distal end, and a primary axis extending colinearly from the distal end of the longitudinal wire member; a rotatable transverse member coupled to the distal end of the longitudinal wire member; an actuation member coupled to the proximal end of the longitudinal wire member; and a retaining member comprising a proximal end and a distal end. In particular embodiments, the retaining member is configured to retain the longitudinal wire member; and the actuation member is configured to rotate the distal end of the longitudinal wire member and the rotatable transverse member about the primary axis of the longitudinal wire member.

In some embodiments, the actuation member is configured to laterally translate the distal end of the longitudinal wire member and the rotatable transverse member in a direction collinear with the primary axis of the longitudinal wire member. In specific embodiments, the retaining member is a tubular member comprising a wall extending around a central aperture. In certain embodiments, the wall of the retaining member comprises a relief extending along the retaining member. In particular embodiments, the longitudinal wire member is retained within the relief without obstructing the central aperture. In some embodiments, the device further comprises a handle coupled to the actuation member and coupled to the rotation member. Specific embodiments further comprise a guide member coupled to the handle, where the guide member extends from the handle to the retaining member, and the longitudinal wire member extends through the guide member.

In certain embodiments, the retaining member comprises a slot through the wall, and the guide member extends into the slot. In particular embodiments, the longitudinal wire member extends from the actuation member, through the guide member, and into the relief of the retaining member. In some embodiments, the longitudinal wire member comprises a curved portion at the distal end. In specific embodiments, the rotatable transverse member comprises a slot, and the slot is configured to receive the curved portion of the longitudinal wire member. In certain embodiments, the distal end of the retaining member is angled at a first angle with respect to the primary axis of the longitudinal wire member, and the curved portion of the longitudinal wire member is angled with respect to the distal end of the longitudinal wire member at the first angle.

Particular embodiments further comprise a coupling member configured to couple the device to the elongated instrument. In some embodiments, the coupling member comprises a first aperture configured to extend around the elongated instrument. In specific embodiments, the coupling member is configured to constrain lateral and rotational movement of the device relative to the elongated instrument during use. In certain embodiments, the coupling member comprises an elastic material and an extension configured to allow a user to place the first aperture around a portion of the elongated instrument. In particular embodiments, the coupling member further comprises seal extending around a second aperture of the coupling member and wherein the seal is configured to seal the proximal end of the retaining member. Some embodiments further comprise a seal configured to seal the proximal end or the distal end of the retaining member. In specific embodiments, the retaining member comprises a clip configured to couple the longitudinal wire member to the elongated instrument such that the longitudinal member and the transverse member can move relative to the surface of the elongated instrument.

In certain embodiments, the device is configured for use in a bodily cavity, in-vivo. In particular embodiments, the device is configured for use in an earthly cavity, in-ground. In some embodiments, the device is configured for use in a man-made construction cavity. In specific embodiments, the ribbon member is configured to remove matter from the surface of the elongated instrument. In certain embodiments, the matter includes liquid matter. In particular embodiments, the matter includes solid matter. In some embodiments, the matter includes viscous fluid. In specific embodiments, the device is configured to provide for liquid or surfactant delivery for cleaning the surface of the elongated instrument.

In certain embodiments, the rotatable transverse member comprises a polymer coating or surface treatment. In particular embodiments, the polymer coating or surface treatment results in reduced adhesion of particulate matter to the surface of the device. In some embodiments, the rotatable transverse member is formed from a polymer material. In specific embodiments, the rotatable transverse member comprises a deformable material. In certain embodiments, the deformable material is selected from the group consisting of rubber, foam, and fabric. In particular embodiments, the deformable material is selected from the group consisting thermoplastic polyurethane (TPU), thermoplastic elastomer (TPE), or medical grade silicone. In some embodiments, the thermoplastic polyurethane (TPU), thermoplastic elastomer (TPE), or medical grade silicone are overmolded or insert molded. In specific embodiments the rotatable transverse member is perpendicular to the longitudinal wire member. In certain embodiments, the rotatable transverse member is angled with respect to the longitudinal wire member. In particular embodiments, the retaining member is a multi-lumen tube.

Certain embodiments include a method of cleaning a surface of a distal end of an elongated instrument, where the method comprises positioning a cleaning device proximal to the elongated instrument, and where the cleaning device comprises: a longitudinal wire member comprising a proximal end, a distal end, and a primary axis extending colinearly from the distal end; a rotatable transverse member coupled to the distal end of the longitudinal wire member; and a retaining member. Particular embodiments comprise positioning the distal end of the longitudinal wire member proximal to the distal end of the elongated instrument; engaging the rotatable transverse member with the surface of the distal end of the elongated instrument; and rotating the rotatable transverse member across the surface of the distal end of the elongated instrument.

In certain embodiments, positioning the cleaning device proximal to the elongated instrument comprises pushing the elongated instrument toward the distal end of the longitudinal wire member. In particular embodiments, positioning the cleaning device proximal to the elongated instrument comprises pulling the proximal end of the longitudinal wire member. In some embodiments, the proximal end of the longitudinal wire member is coupled to an actuation member, and pulling the proximal end of the longitudinal wire member comprises pulling the actuation member. In specific embodiments, rotating the rotatable transverse member across the surface of the distal end of the elongated instrument comprises rotating the actuation member in a first direction.

In certain embodiments, rotating the rotatable transverse member across the surface of the distal end of the elongated instrument comprises rotating the actuation member in a second direction opposite of the first direction. In particular embodiments, the surface of the distal end of the elongated instrument is not flat. In some embodiments, the distal end of the elongated instrument comprises a raised surface around the perimeter of the distal end. In specific embodiments, the device is configured for use in a bodily cavity, in-vivo. In certain embodiments, the device is configured for use in an earthly cavity, in-ground. In some embodiments, the device is configured for use in a man-made construction cavity. In specific embodiments, the rotatable transverse member is configured to remove matter from the surface of the elongated instrument. In particular embodiments, the matter includes liquid matter. In certain embodiments, the matter includes solid matter. In particular embodiments, the matter includes viscous fluid.

This application may implement materials including one or multiple types of cleaning components, such as deformable, flexible, and/or absorbent components (i.e. rubber, bristles, sponges, etc.) (will be referred to as "components" for the remainder of this document). These components may allow for the cleaning of the scope without any further addition. These components may also provide for enhanced cleaning with the inclusion of additional cleaning material, such as a cloth, foam, sponge, ribbon, etc. (will be referred to as "ribbon member" for the remainder of this document). This cloth may have a material or geometrical alteration for improved cleaning performance (e.g. napped/fuzzy surface, microfiber structure, ideal porosity and absorbance) in addition to improved interaction with the rest of the device (distal, proximal, and base ends of device) (e.g. ideal friction relationship, thickness for trocar compatibility, etc.).

As these aforementioned components deform, they allow for the ribbon to conform about the scope surface, applying an adequate force/pressure on the ribbon to improve cleaning efficacy of the ribbon. As the components deform, their deformation may prove two-fold in application, as they (1) store energy, and generate higher cleaning forces/pressures on the surface (possibly translated via a ribbon) and (2) allow for more ideal conformation and improve force/pressure distribution to the surface, and possibly allow for more ideal conformation and improve force/pressure distribution of a cleaning ribbon to the surface.

It should be noted that the ribbon itself may act as its own deformation component or compressible member if its structure allows for it. This could include its material or geometrical configuration. It has been shown that altering its contact approach (e.g. parallel vs. perpendicular, flat vs. twisted orientation, etc.) can alter cleaning performance and interaction performance with the rest of the device.

It should also be noted that the ribbon member may be a belt that cycles on a single spool or it may be fed by one spool, in one direction, and received by a different spool (e.g. one spool feeds ribbon while another spool receives ribbon). These spools may be on the same shaft, or a different shaft. These spools, and/or the ribbon, may be held with tension that allows for potentially more convenient device interfacing, or held with slack, allowing for potentially improved conformation to scope surface. Actuation of the spools may be controlled by the user, or may be automated. It is important to recognize that the inclusion of tension in the ribbon may alter cleaning performance, as the contact points of the ribbon on the scope may actually cause the ribbon to reduce contact/contact force on the scope surface. This highlights the importance of the aforementioned components, and their ability to conform to the scope surface (possibly via/translated to the ribbon).

The aforementioned components may or may not be soaked/coated in a solution that assists in the removal of unwanted objects, contaminants, particles, etc. from the surface of the elongated instrument that is to be cleaned. Delivery of this solution may be actively controlled by the user, or passively controlled by the cleaning actuation mechanism. This solution may be housed in the cleaning tip, along or inside the proximal member, or at the base of the proximal member, or all of the above. This solution may or may not be a saline solution, or a surfactant solution that appropriately and adequately removes bodily fluids and tissues from the surface, including but not limited to condensation, blood, interstitial fluid, fat tissue, etc.

In another embodiment, a cut may be made in the wall of the proximal member. This cut may alter the geometry of the proximal member to allow for storage of energy, and translation/rotation of the proximal tip. One example is a slit on a single side of the distal tip. When the scope contacts the components/ribbon in the distal tip, energy storage occurs, and eventually, the geometry and energy storage/release causes the distal member to deflect/fall out of view of the surface, allowing for the surgeon to see again. Another example is the cut of a spring-like geometry into the proximal member. This geometrical cut operates similarly to the single slit, but also allows for improved energy storage, in addition to a torsional/rotational motion that is translated to the distal tip, potentially increasing surface coverage. Additionally, the tip itself may be made into a coil-spring geometry after geometrical cuts and potential forming techniques, offering comparable benefits as previously explained.

In another embodiment, an elastic component may drag over the scope surface to allow for energy storage, component deformation, and improved cleaning via applied force/pressure and conformation to surface. This elastic component may/may not have a ribbon included, for reasons and interactions previously mentioned. It is worth noting that if a ribbon is included, the tensioning, or even the cycling of a slack ribbon, when interacting with this elastic component, may lead to the stretching of the elastic component. This means that actuation could be made separate from contact, as was described in previously mentioned embodiments. It should be noted that such an actuation could also be included in previous embodiments, with proper integration of this elastic component.

Exemplary embodiments of the present disclosure fit around or beside the laparoscope and inside a trocar port. The scope is retracted back until it is a set/particular distance above the aforementioned components/ribbon/combination. It is then pushed into contact with and eventually passed the components/ribbon/combination, and cleaning may occur. The cleaning may occur within this passively actuated cleaning event. During this cleaning event, the ribbon, if included, may be held "fixed" relative to the spool/components, and still allow cleaning. The ribbon would be rotated/cycled/fed either before or after each cleaning event. Alternatively, the ribbon may be actively rotated/cycled/fed during the cleaning event (i.e. the ribbon is rotated as it comes into contact and eventually passes the aforementioned components. It has been shown that the latter method may prove to be a more effective cleaning approach (i.e. extended pressure with new cleaning material passing over scope) while the former method may still clean effectively with a minimal number of actuations (currently estimated 1-5 actuations), though may stand to be less repeatable and reliable, when compared to the latter method.

Both of these aforementioned mechanical embodiments are unique and different from current technology due at least in part to the fact that the cleaning mechanisms and/or combinations of mechanisms have unique geometric and/or material and/or orientation (arguably geometrical as well) specifications that are key to its performance. This is especially important and novel due to the fact that a single configuration (primarily relating to inner diameter) of the present disclosure can clean multiple styles of laparoscopes (e.g. different angles) at the same efficiency—e.g. flat scopes, 300 scopes, 450 scopes, etc. Current technologies do not appear to allow for this.

Exemplary embodiments of the present disclosure are compatible with current laparoscope-trocar pairings. Current technology does not appear to allow for this. For example, a 5 mm laparoscope (approximately 5.0-5.5 mm diameter) fits inside a common 5 mm trocar port (approximately 7.1 mm diameter). Current technology seems to require a larger port. Exemplary embodiments of the present disclosure, due to novel and elegant mechanisms, can be made to fit within those smaller tolerances.

One mechanical embodiment utilizes high frequency vibration either onto the laparoscope directly, or onto a mechanical component that in turn vibrates the laparoscope at a high frequency. One optical embodiment utilizes optical intensity, frequency, continuous and/or pulsed light methods to remove debris from the surface. These light parameters can be altered via an attachment, or a built-in system.

Certain embodiments utilize a longitudinal member and a transverse member at the distal (surface) end of the laparoscope to be moved (e.g. swept, dragged, rotated, etc.) across the surface. In such embodiments, the transverse member may or may not be soaked or coated in a solution that assists in the removal of unwanted matter (e.g. objects, contaminants, particles, etc.) from the surface of the laparoscope. In certain embodiments, the solution may or may not be a saline solution, or a surfactant solution that appropriately and adequately removes bodily fluids and tissues from the surface, including but not limited to condensation, blood, interstitial fluid, fat tissue, etc.

Certain embodiments may implement surface cleaning materials, including one or multiple types of transverse members, such as flexible and/or absorbent components such as bristles, wipers, or sponges, with a longitudinal member configured as an elongated tube, rod, bar, or sheet. In some embodiments, the tube or rod fits around the laparoscope and inside a trocar. The distal end of the tube or rod can hold or house the transverse member (or members) that act as cleaning components. The scope can then be positioned (i.e. the scope retracted back or the tube or rod pushed forward) until it is a specific distance above the aforementioned cleaning components. The scope can then be pushed into and past the transverse member(s), which can perform a majority of the cleaning, at effective forces due to the stiffness and/or material properties of the transverse member(s), and the total combined surface area coverage.

In certain embodiments, an absorbent or sponge material may be implemented at the distal end of the longitudinal member to absorb or clean any remaining droplets or particles of elements that were not removed via the transverse member, if necessary. Exemplary embodiments of the device can clean different angled scopes of similar diameters with comparable efficacy.

Exemplary embodiments of the present disclosure comprise cleaning mechanisms and/or combinations of mechanisms with unique geometric, material and/or orientation specifications that provide the ability to effectively remove matter from an elongated instrument surface held within a cavity.

In particular embodiments, a single configuration of the device can clean multiple styles of laparoscopes (e.g. different angles such as flat scopes, 30 degree scopes, 45 degree scopes and 70 degree scopes) at a relatively equivalent efficiency.

Exemplary embodiments are also compatible with current common laparoscope-trocar pairings, in contrast to typical existing systems. For example, a 5 mm laparoscope (approximately 5.0-5.5 mm diameter) can fit within a common 5 mm trocar port (approximately 7.1 mm diameter). Current systems can require a larger port, while exemplary embodiments of the device disclosed herein can be made to fit within these tolerances.

Certain embodiments utilize one or more geometrical rubber/foam mats/wipers fixed to the distal end of the device. As a scope is retracted into the sheath, the rubber wiper comes to rest in a passive position. As the scope is then pushed forward into the rubber wiper, the geometry and material of the wiper, in addition to its positioning relative to the scope surface allows the wiper to "scrape", slide, or drag across the surface, comparable to that of a windshield wiper.

Certain embodiments utilize high frequency vibration either onto the laparoscope directly, or onto a mechanical component that in turn vibrates the laparoscope at a high frequency. Particular embodiments utilize optical intensity, frequency, continuous and/or pulsed light methods to remove debris from the surface. These light parameters can be altered via an attachment, or a built-in system.

Certain exemplary embodiments comprise a sheath that fits around a laparoscope or other type of cylindrical or tubular device that might require cleaning at a distal end (i.e. an endoscope). Particular embodiments include a transverse member that functions as a cleaning mechanism at the distal end of the device. In specific embodiments, the cleaning mechanism may comprise a hook-like, claw-like, broom-like, squeegee-like, or scraper-like geometry or configuration. During operation of exemplary embodiments, a component at a distal end of the transverse member is drawn across the surface, thereby cleaning debris from the surface.

In particular embodiments, the transverse member may be formed from a material comprising (or include a coating comprising) rubber, foam, plastic, or cloth material that does not scratch, harm, or impede the surface to be cleaned. In certain embodiments, the transverse member may include bristles, wipers, or an absorbent material (e.g. a material that is foam or sponge-like in nature). In specific embodiments, the transverse member may include a particular surface texture, including for example a surface finish of 0.01 microns-1000 microns, or more particularly 0.1-100 microns, or more particularly 1.0-10 microns.

In specific embodiments, the transverse member may include a surface porosity of 0-75 percent porosity, or more particularly 10-50 percent porosity, or more particularly 20-35 percent porosity.

In specific embodiments, the transverse member may include a particular rigidity, resilience, and/or flexibility to promote effective matter removal from the surface of the elongated instrument. In certain embodiments, the material of the transverse member may have an elastic modulus of 0.005-5 gigapascals (GPa), or more particularly 0.05-2.0 GPa, or more particularly 0.5-1.5 GPa.

In some embodiments, the distal end of the transverse member may comprise a particular geometry of the cleaning edge (e.g., sharpened, rounded, multi-pronged, etc.). In certain embodiments, the transverse member may include particular component angles and radii of approach and implementation where the transverse member is coupled to the longitudinal member (which may be configured as a sheath). For example, the angle between the transverse member proximal end and the longitudinal member may be between 0-90 degrees, or more particularly between 15 and 60 degrees, or more particularly between 30 and 45 degrees. In addition, the angle between the transverse member distal end and the surface to be cleaned may be between 0-180 degrees, or more particularly between 15 and 135 degrees, or more particularly between 30 and 90 degrees or more particularly between 45 and 60 degrees.

In addition, the transverse member can be configured so that it is able to remain out of view of the elongated instrument, including adjacent to or near the elongated instrument, as the user desires.

During operation of the device, it can expel dirty material from the surface and/or cleaning surface of the transverse member. Certain embodiments may also include an additional mechanism with the ability to convert stored potential energy to kinetic energy, including for example, a vibrational or "flick" mechanism. In certain embodiments, such a mechanism could be activated after transverse member initially moves across the surface of the elongated instrument.

In certain laparoscopic embodiments, the device can be configured such that it is compatible with current commonly paired apparatus (e.g. a 5 mm diameter laparoscope with a commonly paired trocar). In certain embodiments, the device may be used in conjunction with an elongated instrument having a shaft with a diameter of approximately 2.7 mm-approximately 12.0 mm and a trocar having a diameter of approximately 3.0 mm-13.0 mm.

In particular embodiments, the device may include a transverse member that is curved and has a radius of curvature of 1.3 mm-12.5 mm, or more particularly 2.0 mm-10.0 mm, or more particularly 3.0 mm-9.0 mm, or more particularly 4.0 mm-8.0 mm, or more particularly 5.0 mm to 7.0 mm. In specific embodiments, the device may include a longitudinal member that is tubular and had a diameter between approximately 3.0 mm and approximately 13.0 mm.

In certain embodiments, the device may comprise a constraint that aligns the transverse member appropriately with the surface of the elongated instrument to be cleaned. This can be particularly important for compatibility with different angled surfaces. Exemplary embodiments can be actuated easily and quickly by manual or automated means, potentially via human input, robotic or mechanical input, or pneumatic input.

Exemplary embodiments include a device configured to clean a surface of an elongated instrument held within a cavity. In certain embodiments, the device comprises a longitudinal member comprising a proximal end and a distal end, and a flexible transverse member comprising a proximal end and a distal end, where the proximal end of the flexible transverse member is coupled to the distal end of the longitudinal member. In particular embodiments, the distal end of the flexible transverse member is spaced apart or biased away from the proximal end of the transverse member, and the flexible transverse member is configured such that the distal end of the flexible transverse moves away from the longitudinal member (and/or moves away from the proximal end of the flexible transverse member) when a surface at an angle to the longitudinal member exerts a force on the distal end of the flexible transverse member in a direction parallel to the longitudinal member.

In some embodiments, the distal end of the flexible transverse member is configured to remove matter from the surface when the distal end of the flexible transverse moves away from the longitudinal member. In specific embodiments, the matter includes liquid matter (including for example, viscous fluids), or solid matter, or both liquid and solid matter. In certain embodiments, the surface is generally perpendicular to the longitudinal member, and in particular embodiments the surface is at an angle of approximately up to seventy degrees from the longitudinal member. In some embodiments, the longitudinal member is a tubular member, and in specific embodiments the tubular member has a diameter of between approximately 3.0 mm-and approximately 13.0 mm. In certain embodiments, the longitudinal member is a planar member. In particular embodiments, the longitudinal member and the flexible transverse member are formed from a unitary component, and in some embodiments, the longitudinal member and the flexible transverse member are separate components.

In specific embodiments, the flexible transverse member is curved or planar, and in certain embodiments has a radius of curvature of between approximately 1.3 mm-and approximately 12.5 mm. In particular embodiments, the flexible transverse member is formed from a plastic material, and in some embodiments the flexible transverse member comprises a deformable material coating, including for example, rubber, foam, fabric, or Velcro®. In some embodiments, the flexible transverse member comprises an extension member, and in specific embodiments the extension member is coupled to the distal end of the flexible transverse member. In certain embodiments, the extension member is angled toward the longitudinal member, and in particular embodiments, the flexible transverse member is a tubular member.

Specific embodiments include a system for cleaning a surface of an elongated instrument held within a cavity, where the system comprises: a longitudinal member comprising a proximal end and a distal end; a transverse member coupled to the distal end of the longitudinal member; and an elongated instrument comprising a shaft and a distal end of the shaft. In certain embodiments, the longitudinal member is configured to extend along the shaft of the elongated instrument; the transverse member is biased toward the shaft of the elongated instrument when the elongated instrument is positioned in a first position such that a first distance between the surface and the proximal end is greater than a second distance between the transverse member and the proximal end; and the transverse member is configured to extend across the surface when the elongated instrument is positioned in a second position such that the first distance between the surface and the proximal end is equivalent to the second distance between the transverse member and the proximal end.

In certain embodiments of the system, the distal end of the transverse member translates across the surface while maintaining contact with the surface as the longitudinal member is retracted back toward the proximal end of the elongated instrument (or as the elongated instrument is advanced relative to the longitudinal member). In particular embodiments, the transverse member is configured to retract across the surface when the elongated instrument is moved from the second position to a third position such that a third distance between the surface and the proximal end is greater than the second distance between the transverse member and the proximal end. In some embodiments, the transverse member is configured to remove matter from the surface when the transverse member retracts across the surface. In specific embodiments, the matter includes liquid matter (including for example, viscous fluids), or solid matter or both liquid and solid matter. In certain embodiments, the longitudinal member is a tubular member, and in particular embodiments, the longitudinal member is a planar member.

In particular embodiments of the system, the longitudinal member and the transverse member are formed from a unitary component, and in some embodiments the longitudinal member and the transverse member are separate components. In some embodiments, the transverse member is curved or planar, and in specific embodiments the transverse member has a radius of curvature of between approximately 1.3 mm-and approximately 12.5 mm.

Certain embodiments include a device configured to clean a surface of an elongated instrument held within a cavity, where the device comprises: a longitudinal member comprising a proximal end and a distal end; a first flexible transverse member; and a second flexible transverse member. In particular embodiments, the longitudinal member is a tubular member; the first flexible transverse member extends across the distal end of the longitudinal member: the second flexible transverse member extends across the distal end of the longitudinal member; and the first and second flexible members are configured to move across a surface at an angle to the longitudinal member when the surface moves past the distal end of the longitudinal member. In some embodiments, the surface is a lens of an elongated instrument, and in specific embodiments the first flexible member is parallel to the second flexible member and the first flexible member is spaced apart from the second flexible member.

Exemplary embodiments include a method of cleaning a surface of an elongated instrument held within a cavity, where the method comprises positioning a device adjacent to the elongated instrument held within a cavity, where the device comprises a longitudinal member and a flexible transverse member, the flexible transverse member comprises a proximal end coupled to the longitudinal member, the flexible transverse member comprises a distal end, and the flexible transverse member is located adjacent the surface of the elongated instrument. Exemplary embodiments of the method further comprise changing a relative position of the device and the elongated instrument, where the distal end of the flexible transverse member engages the surface of the elongated instrument, and the distal end of the flexible transverse member moves across the surface of the elongated instrument.

In certain embodiments of the method, the elongated instrument is a laparoscope, and in particular embodiments the surface of the elongated instrument is a lens. In some embodiments, the distal end of flexible transverse member moves toward the proximal end of the flexible transverse member when the distal end of the flexible transverse member moves across the surface of the elongated instrument. In specific embodiments, the distal end of the flexible transverse member removes matter from the surface of the elongated instrument when the distal end of the flexible transverse moves across the surface of the elongated instrument.

In certain embodiments of the method, the matter includes liquid matter (including for example, viscous fluids), or solid matter or both liquid and solid matter. In particular embodiments, the surface of the elongated instrument is generally perpendicular to the longitudinal member. In some embodiments, the surface of the elongated instrument is at an angle of approximately forty-five degrees from the longitudinal member. In specific embodiments, the longitudinal member is a tubular member, and in certain embodiments the tubular member has a diameter of between approximately 3.0 mm- and approximately 13.0 mm.

In particular embodiments of the method, the longitudinal member is a planar member. In some embodiments, the longitudinal member and the flexible transverse member are formed from a unitary component and in specific embodiments the longitudinal member and the flexible transverse member are separate components. In certain embodiments, the flexible transverse member is curved or planar, and in particular embodiments the flexible transverse member has a radius of curvature of between approximately 1.3 mm-and approximately 12.5 mm. In certain embodiments, the flexible transverse member is formed from a plastic material. In particular embodiments, the flexible transverse member comprises a coating is selected from the group consisting of rubber, foam and fabric.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "approximately, "about" or "substantially" mean, in general, the stated value plus or minus 10%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
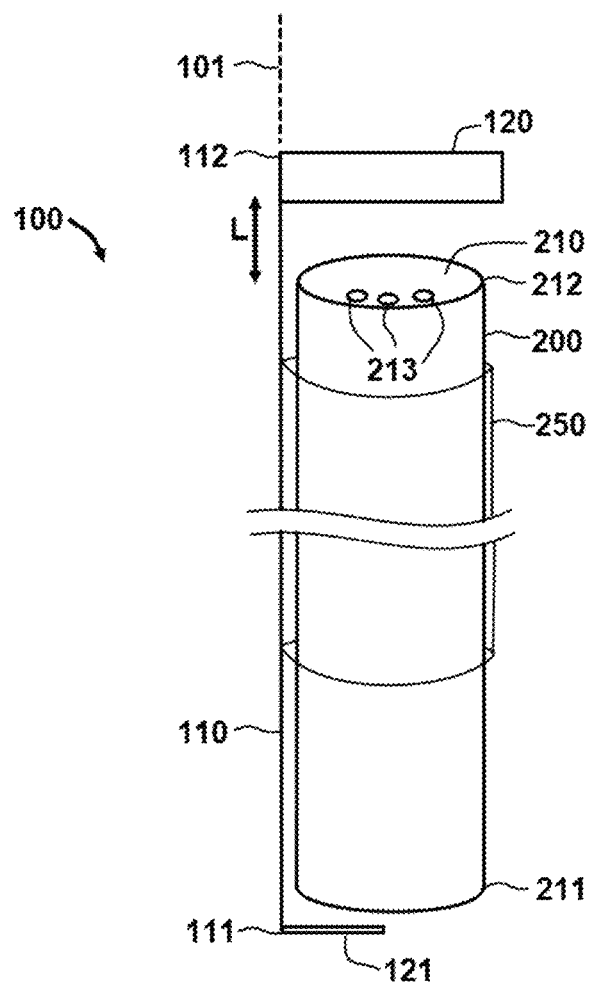
FIGS. 1-3 illustrate a schematic of a device according to an exemplary embodiment of the present disclosure during use.
Figure 2:
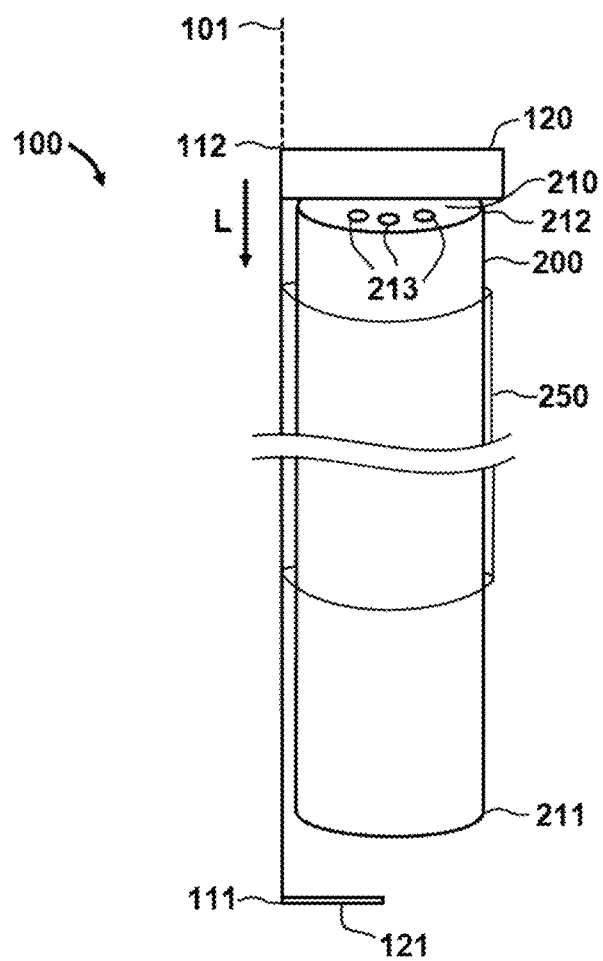
Figure 3:
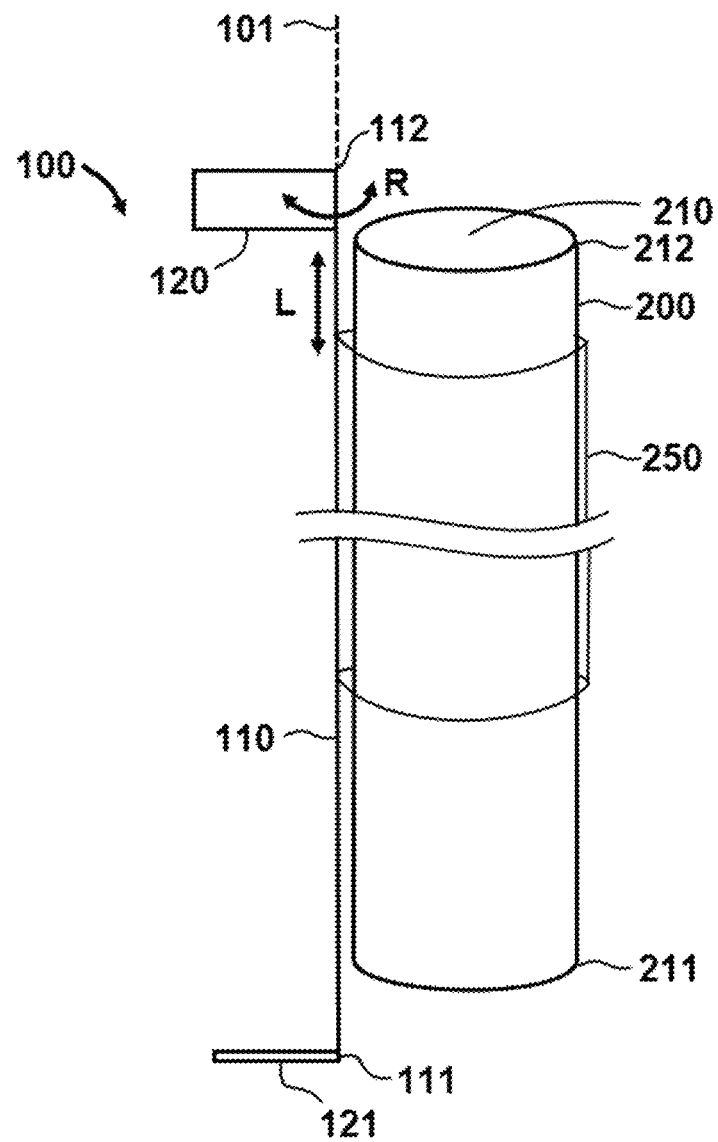

Referring now to FIGS. 1-3, schematic views of an exemplary embodiment of a device 100 is shown during use cleaning an elongated instrument 200. In the embodiment shown, device 100 is configured to clean a surface 210 of elongated instrument 200 held within a cavity (e.g. in a bodily cavity vivo or in an earthly cavity in-ground). In certain embodiments surface 210 may be a lens and elongated instrument 200 may be a laparoscope. In the illustrated embodiment, elongated instrument 200 comprises a proximal end 211 and distal end 212. In this embodiment, device 100 comprises a longitudinal wire member 110 comprising a proximal end 111 and a distal end 112. Device 100 also comprises a rotatable transverse member coupled to distal end 112 of longitudinal wire member 110. As used herein, distal end 112 of longitudinal wire member 110 comprises a region of longitudinal member 110 that is distal from the absolute end of longitudinal wire member 110. Accordingly, a portion (e.g. 5 or 10 percent) of longitudinal wire member 110 may extend beyond the coupling point of rotatable transverse member 120 and longitudinal wire member 110 (e.g. may extend away from distal end 112). In certain embodiments, longitudinal wire member 110 and rotatable transverse member 120 may be formed from a unitary component, while in other embodiments, longitudinal wire member 110 and rotatable transverse member 120 may be separate components. In exemplary embodiments, longitudinal wire member 110 is configured as a long, thin, member that allows rotation of distal end 112 upon rotation of proximal end 111. Exemplary embodiments of longitudinal wire member 110 comprise metallic and non-metallic materials, including for example composite, plastic or other polymer materials.

In the embodiment shown, device 100 comprises a retaining member 250 configured to retain a component of device 100 (e.g. longitudinal wire member 110 in the embodiment shown) to elongated instrument 200. In this embodiment, retaining member 250 is shown as a tubular member or sheath that is coupled to device 100 and extends around elongated instrument 200. In certain embodiments, retaining member 250 may be configured as a multi-lumen tube. It is understood that in other embodiments, retaining member 250 may include other configurations, including for example, clips, wires, etc. As explained in further detail below, retaining member 250 is configured to allow sliding or lateral movement between device 100 and elongated instrument 200 in a direction parallel to an axis 101 that extends colinearly from distal end 112. In addition, retaining member 250 is also configured to allow rotational movement of device 100 about axis 101 to facilitate cleaning matter 213 (e.g. solid or liquid) from surface 210.

The embodiment shown further comprises an indicator 121 coupled to longitudinal wire member 110 near proximal end 111. Indicator 121 can indicate the orientation of rotatable transverse member 120 such that a user can determine the position of transverse member 120 with respect to elongated instrument 210 by viewing indicator 121 while rotating device 100 about longitudinal wire member 110 and axis 101.

In the embodiment shown in FIG. 1, device 100 is shown with distal end 112 and rotatable transverse member 120 extended past surface 210 such that surface 210 is between proximal end 111 and distal end 112 of longitudinal wire member 110. The user can view indicator 121 to align rotatable transverse member 120 so that it is aligned rotationally with elongated instrument 200 (e.g. rotatable transverse member 120 is generally "above" surface 120 in the configuration shown in FIG. 1.) Device 100 and/or elongated instrument 200 can then be moved in the direction of arrow L parallel to axis 101 shown in FIG. 1 such that rotatable transverse member 120 is positioned proximal to surface 210. For example, the user can pull proximal end 111 of longitudinal wire member 110 or push elongated instrument 200 in order position rotatable transverse member 120 proximal to surface 210. In certain embodiments, rotatable transverse member 120 (e.g. the cleaning member or a wiper) can be moved between a stowed position and a use position. The stowed position and the use position are relative to a location of the imaging element of an endoscope when the endoscope is mounted on the apparatus. The use position can be a position in which rotatable transverse member 120 is adjacent to or beyond a terminal end of the endoscope. The stowed position can be a position in which rotatable transverse member 120 is retracted from the use position in a direction toward a user interface body of the apparatus.

As device 100 and/or elongated instrument 200 is moved in this direction, rotatable transverse member 120 eventually engages surface 210 as shown in FIG. 2. The engagement of rotatable transverse member 120 with surface 210 provides tactile feedback to the user through longitudinal member 110 to indicate engagement. For example, the resistance in the relative lateral/axial motion between device 100 and elongated instrument 200 is created when rotatable transverse member 120 engages surface 210. As shown in FIG. 3, the user can then rotate longitudinal wire member 110 and rotatable transverse member 120 about axis 101 in the direction of arrow R to wipe clean surface 210. Indicator 121 can be used to confirm that rotatable transverse member 120 has rotated sufficiently to clean debris from surface 210. In certain embodiments surface 210 is not flat and may comprise a raised surface around the perimeter of the distal end of elongated instrument 200. Such configurations can present challenges to efficient cleaning of surface 210 and emphasize the need for effective cleaning devices and techniques.

It is understood the views shown in FIGS. 1-3 represent schematic representations of one embodiment of the present disclosure. Other embodiments may include additional features and aspects. Referring now to FIGS. 4-13, assembled and exploded views are provided of a particular embodiment of a device 100 configured to clean an elongated instrument having an angled surface at the distal end. Components that are equivalent to previously-described components are identified with equivalent reference numbers. For the sake of brevity and to avoid repetition, equivalent components will not be discussed in detail in the description of this embodiments. An overview of the components and operating principles will be presented initially, followed by more specific discussion of particular features of device 100.

In the embodiment shown, device 100 comprises a handle 300 coupled to an actuation member 320, a guide member 330 and a coupling member 340. Actuation member 320 is coupled to longitudinal wire member 110 and can be used to manipulate longitudinal wire member 110 and rotatable transverse member 120 during use. The general operating principles of this embodiment are equivalent to those of the previously-described embodiment in FIGS. 1-3. During use, an elongated instrument (e.g. a laparoscope in certain embodiments, not shown) can be inserted through retaining member 250, and coupling member 340 can be used to couple device 100 to the elongated instrument. In a particular embodiment, coupling member 340 comprises an elastic material with an aperture 341 (see FIGS. 6 and 11) that can be placed over a light port in a laparoscope to constrain lateral and rotational movement of device 100 relative to the elongated instrument. Coupling member 340 may also comprise a tab or extension 343 to assist is manipulating coupling member 340 during the coupling process to the elongated instrument. For example, a user can grasp extension 343 and pull extension 343 initially in a direction away from aperture 341 until aperture 341 is located proximal to the portion of the elongated instrument to which it will be coupled. Extension 343 can then be pulled in a different direction (e.g. toward distal end 251 of retaining member 250) until aperture 341 has engaged and secured device 100 to the elongated instrument. Extension 343 can then be released by the user.

In certain embodiments, a cavity into which device 100 is inserted may be filled with pressurized gas (e.g. insufflation gas in the abdomen during laparoscopic surgery) to allow for a maintenance of cavity pressure or gas concentration. In particular embodiments, device 100 may comprise a seal that can be located at proximal and/or distal end of the device that creates a seal around the elongated instrument and/or retaining member 250 and prevents leaking of gas from the cavity. This can be done through an elastic component that compresses around scope, passively, but still allows for scope to push through longitudinal member, or it could be done through a compliant foam or rubber port, that can be moved aside as the elongated instrument pushes past the compliant part, and the compliant part forms a seal around the elongated instrument.

In the embodiment shown, coupling member 340 further comprises a second aperture 342 which is aligned with a central aperture 255 of retaining member 250 when device 100 is assembled. A seal 344 extends around aperture 342 and restricts the flow of gas through aperture 255 of coupling member 250. Seal 344 can therefore restrict insufflation gas from escaping the cavity into which device 100 is inserted during use. While seal 344 is shown in this embodiment as a unitary component with coupling member 340, it is understood that in different embodiments seal 344 and coupling member 340 may be separate components. In exemplary embodiments, coupling member 340 and/or seal 344 may be formed from an elastic, foam, or other suitably compliant material. In addition, while aperture 342 is shown as a single aperture, other embodiments may comprise multiple partitions or "leaves" that deflect out of the way and back around the shaft of the elongated instrument as the elongated instrument pushes past aperture 342.

Figure 9:
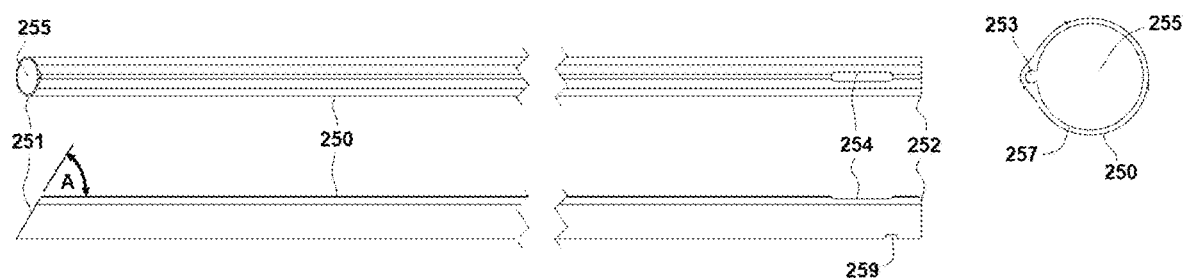
FIG. 9 illustrates orthographic views of a retention member of the embodiment of FIG. 4.

As shown in FIG. 9, retaining member 250 is configured as a tubular member that comprises a wall 257 extending around central aperture 255, as well as a relief 253 (e.g. a semi-circular groove or slot in the illustrated embodiment) in wall 257. Relief 253 extends along retaining member 250 and is sized and configured such that longitudinal wire member 110 is retained in relief 253 without obstructing central aperture 255. Accordingly, relief 253 aligns longitudinal wire member 110 in a straight configuration as it travels the length of retaining member 250. In addition, longitudinal wire member 110 can rotate while being retained within relief 253.

In the embodiment shown, retaining member 250 further comprises a slot 254 through wall 257 and near a proximal end 252 of retaining member 250. Slot 254 is configured to allow guide member 330 (and longitudinal wire member 110) to enter relief 253. In the illustrated embodiment, retaining member 250 further comprises a slot or notch 259 configured to engage a locating rib or tab 258 in handle 300 (shown in FIG. 7) to position or key retaining member 250 to handle 300. The embodiment of retaining member 250 shown in FIG. 9 comprises a distal end 251 that is angled (e.g. to accommodate elongated instruments with angled distal surfaces).

Figure 12:
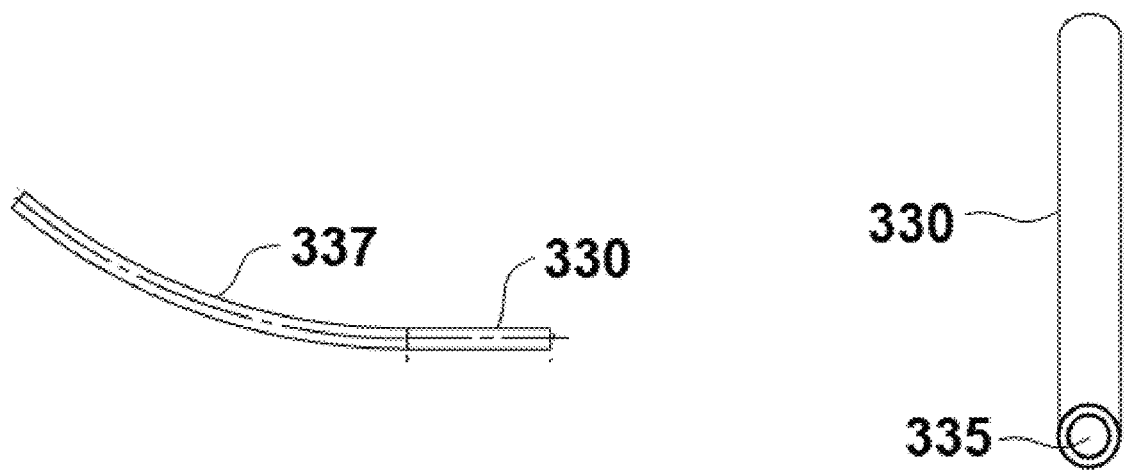
FIG. 12 illustrates orthographic views of a guide member of the embodiment of FIG. 4.

In the embodiment shown in FIG. 12, guide member 330 comprises an aperture 335 through which longitudinal wire member 110 extends. In addition, guide member 330 comprises a curved portion 337 configured to transition longitudinal wire member 110 from actuation member 320, through handle 300 and to retaining member 250. Guide member 330 can further distribute the bending forces exerted on longitudinal wire member 110 and reduce frictional forces as longitudinal wire member 110 is rotated and laterally translated during operation. In specific embodiments, guide member 330 may be formed from 304 or 316 stainless steel, and longitudinal wire member 110 may be formed from 316 stainless steel.

Figure 10:
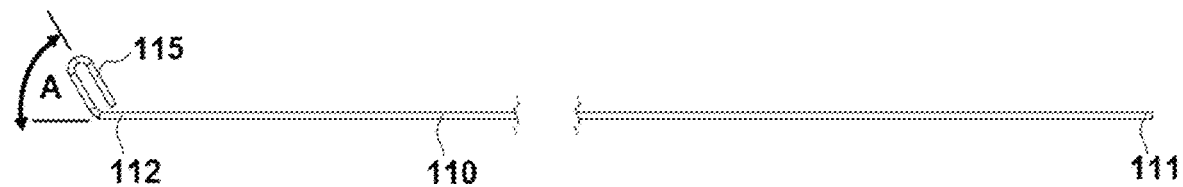
FIG. 10 illustrates a side view of a longitudinal wire member of the embodiment of FIG. 4.
Figure 11:
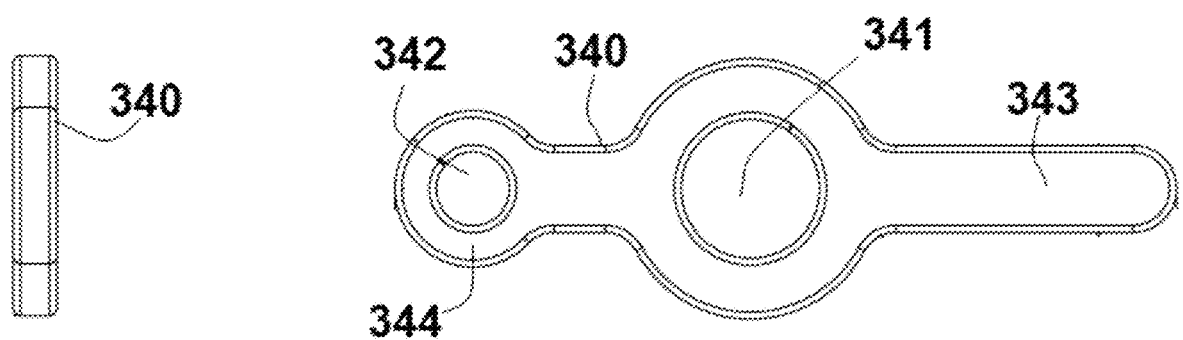
FIG. 11 illustrates orthographic views of a coupling member of the embodiment of FIG. 4.
Figure 13:
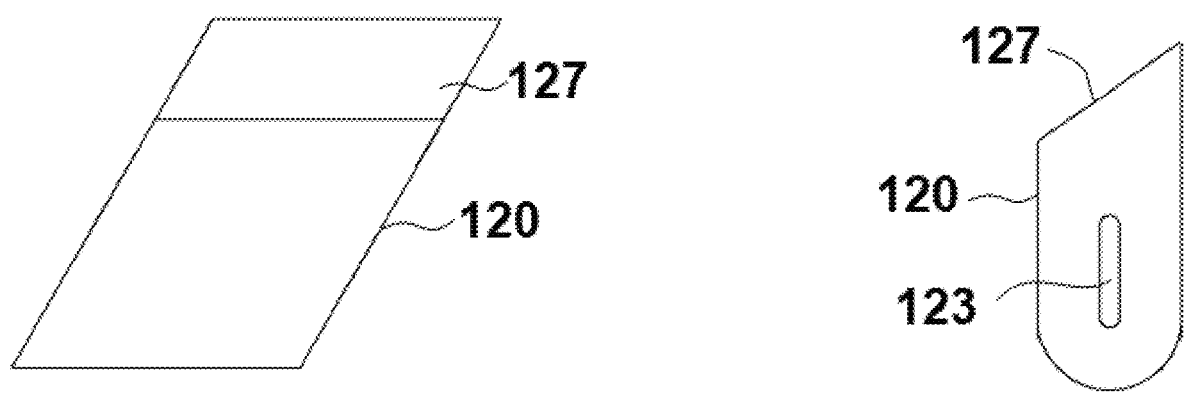
FIG. 13 illustrates orthographic views of a rotatable transverse member of the embodiment of FIG. 4.

In the embodiments shown in FIGS. 10 and 13, longitudinal wire member 110 comprises a curved portion 115 near distal end 112, and rotatable transverse member 120 comprises a slot 123 configured to receive curved portion 115 of longitudinal wire member 110. In the embodiment shown, curved portion 115 is configured at an angle A with respect to distal end 112 that is equivalent to distal end 251 of retaining member 250. In exemplary embodiments, rotatable transverse member 120 is coupled to distal end 112 of longitudinal wire member 110 via a friction fit between slot 123 and curved portion 115. In certain embodiments, rotatable transverse member 120 can be removed and replaced by a user by pulling on rotatable transverse member 120 in a direction parallel to curved portion 115. In the embodiment shown, rotatable transverse member 120 comprises an angled surface 127 configured to provide improved wiping or cleaning action during use. In exemplary embodiments the geometry, contact angle, contact force, and material of construction can be optimized for rotatable transverse member 120 to provide for efficient cleaning of the elongated instrument.

Figure 8:
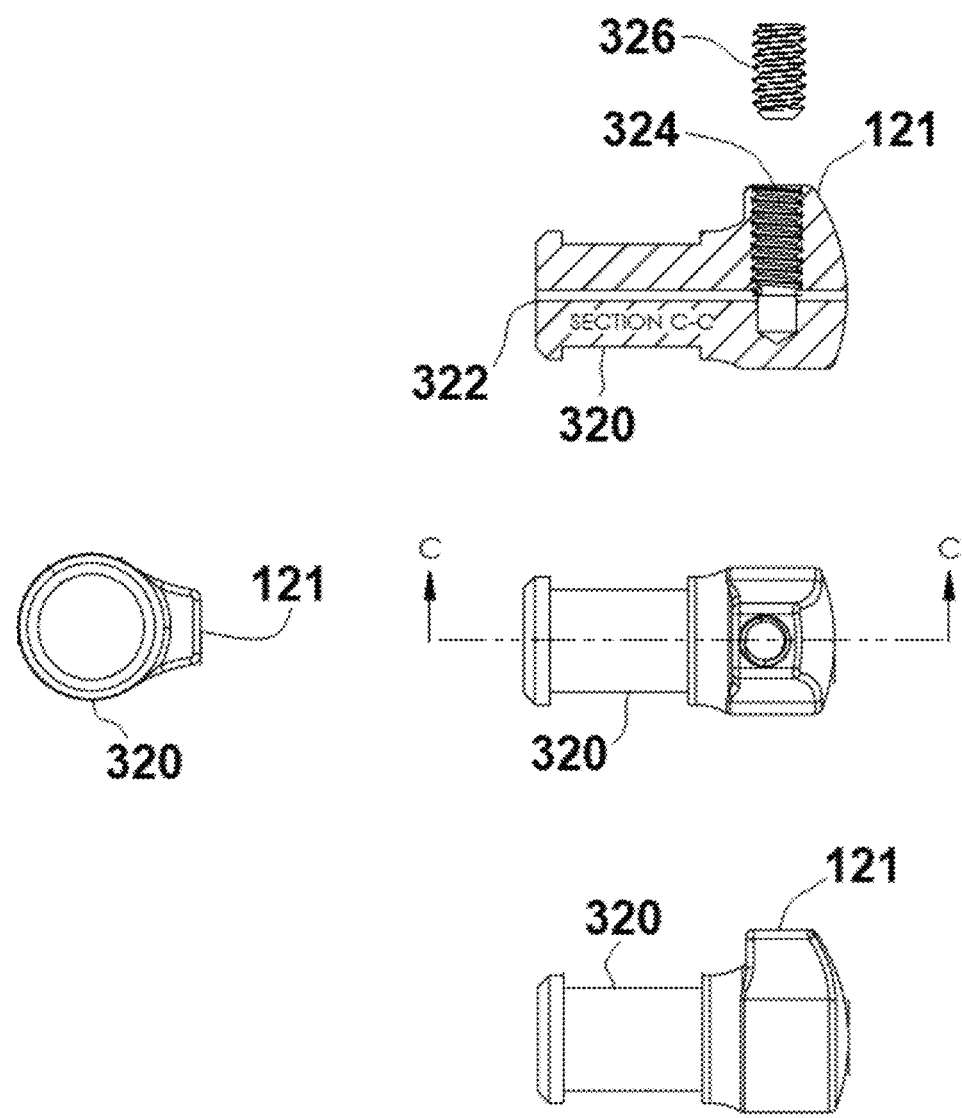
FIG. 8 illustrates section and orthographic views of an actuation member of the embodiment of FIG. 4.

In the embodiment shown in FIG. 8, actuation member 320 comprises a first aperture 322 configured to receive longitudinal wire member 110. In the embodiment shown, actuation member 320 comprises a second aperture 324 configured to receive a coupling member 326 configured to secure longitudinal wire member 110 to actuation member 320. In the embodiment shown, coupling member 326 is a threaded member, but in other embodiments coupling member 326 may have a different configuration (e.g. a pin, stake, etc.).

Figure 7:
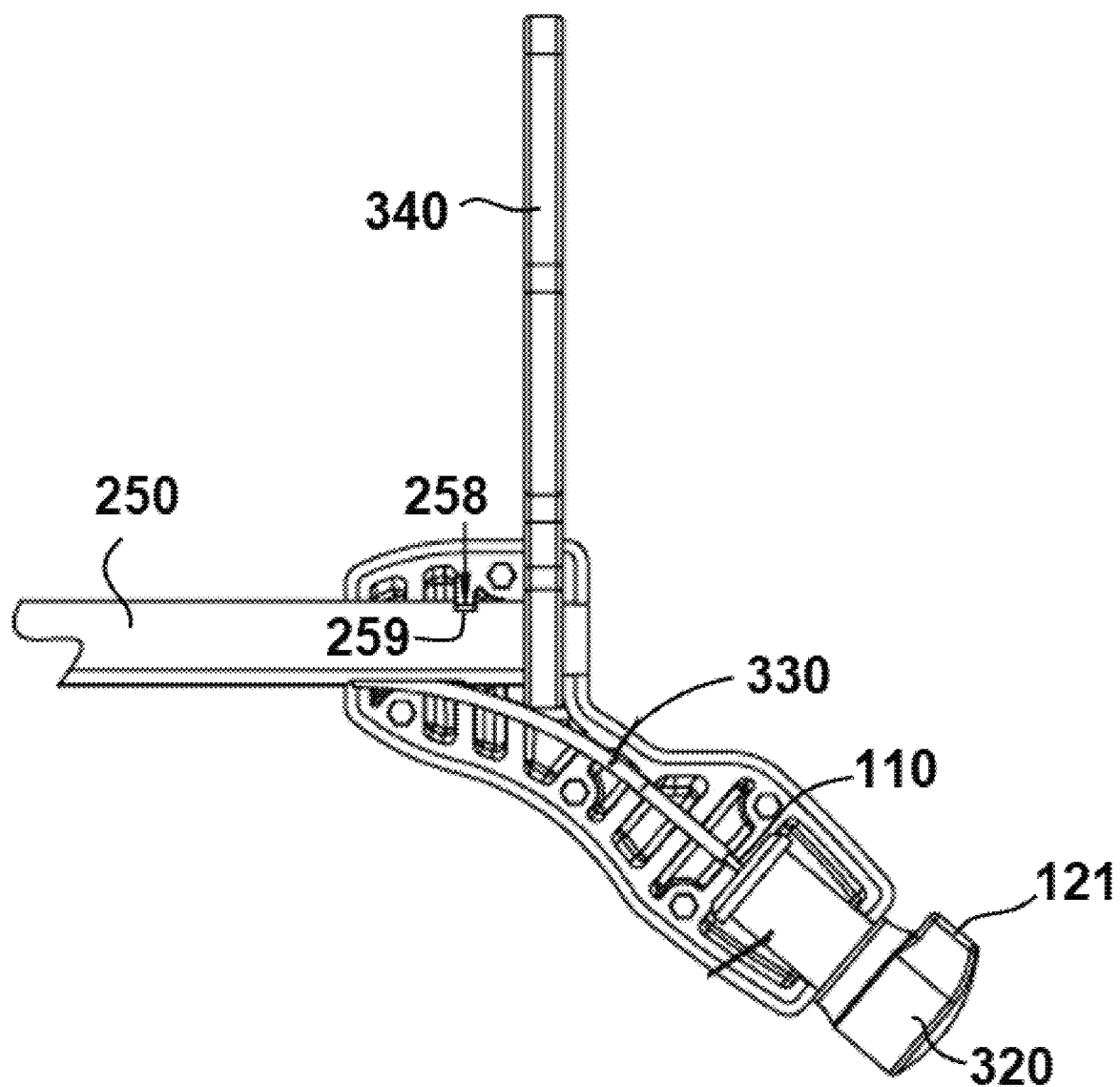
FIG. 7 illustrates a partial section view of the embodiment of FIG. 4

In certain embodiments, device 100 and an elongated instrument can be inserted through a trocar into a cavity of a patient during use. As shown in FIGS. 7 and 8, actuation member 320 comprises an indicator 121 that is aligned with rotatable transverse member 120. A user can initially manipulate actuation member 320 by rotating it such that rotatable transverse member 120 does not extend over the distal end of the elongated instrument and interfere with operation of the elongated instrument. For example, if the elongated instrument is a laparoscope, rotatable transverse member 120 will not block the view of the laparoscope when rotatable transverse member 120 is positioned 180 degrees from the position shown in FIG. 4. However, if matter accumulates on the end of the elongated instrument during use, actuation member 320 can be manipulated to remove the matter and restore the functionality of the elongated instrument.

Figure 4:
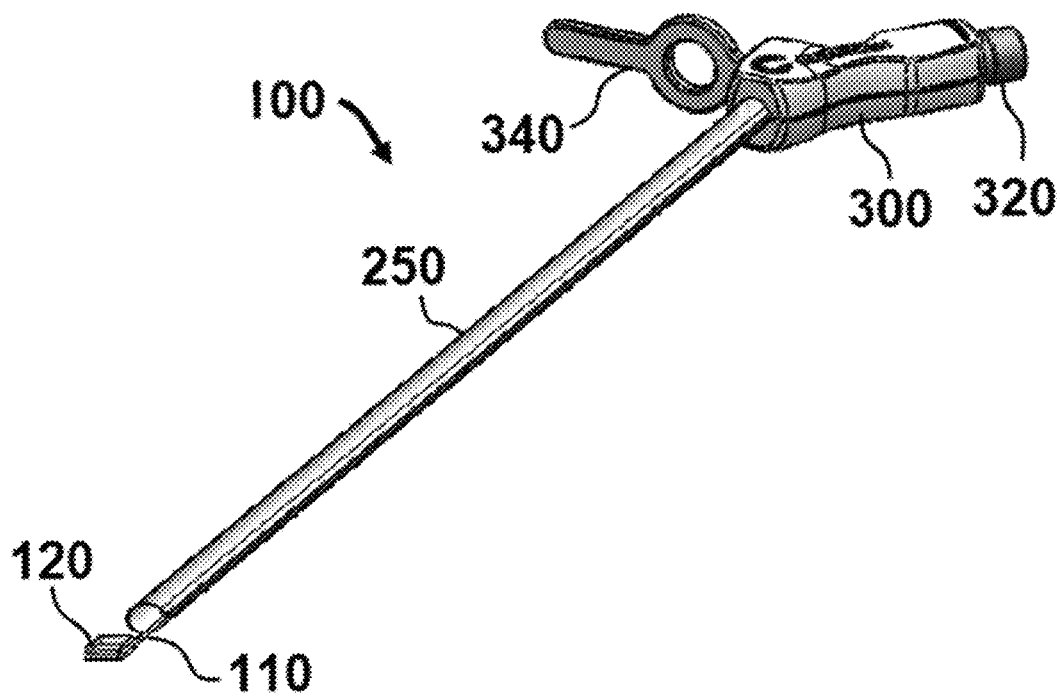
FIG. 4 illustrates a perspective view of a device according to an exemplary embodiment of the present disclosure.
Figure 5:
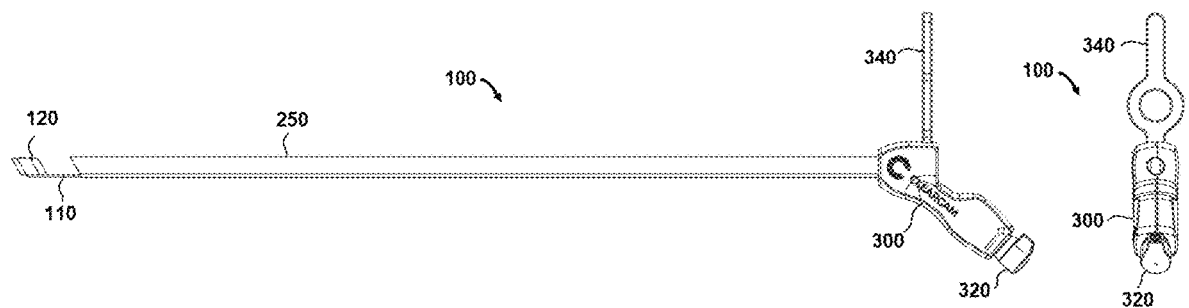
FIG. 5 illustrates a side view and an end view of the embodiment of FIG. 4.
Figure 6:
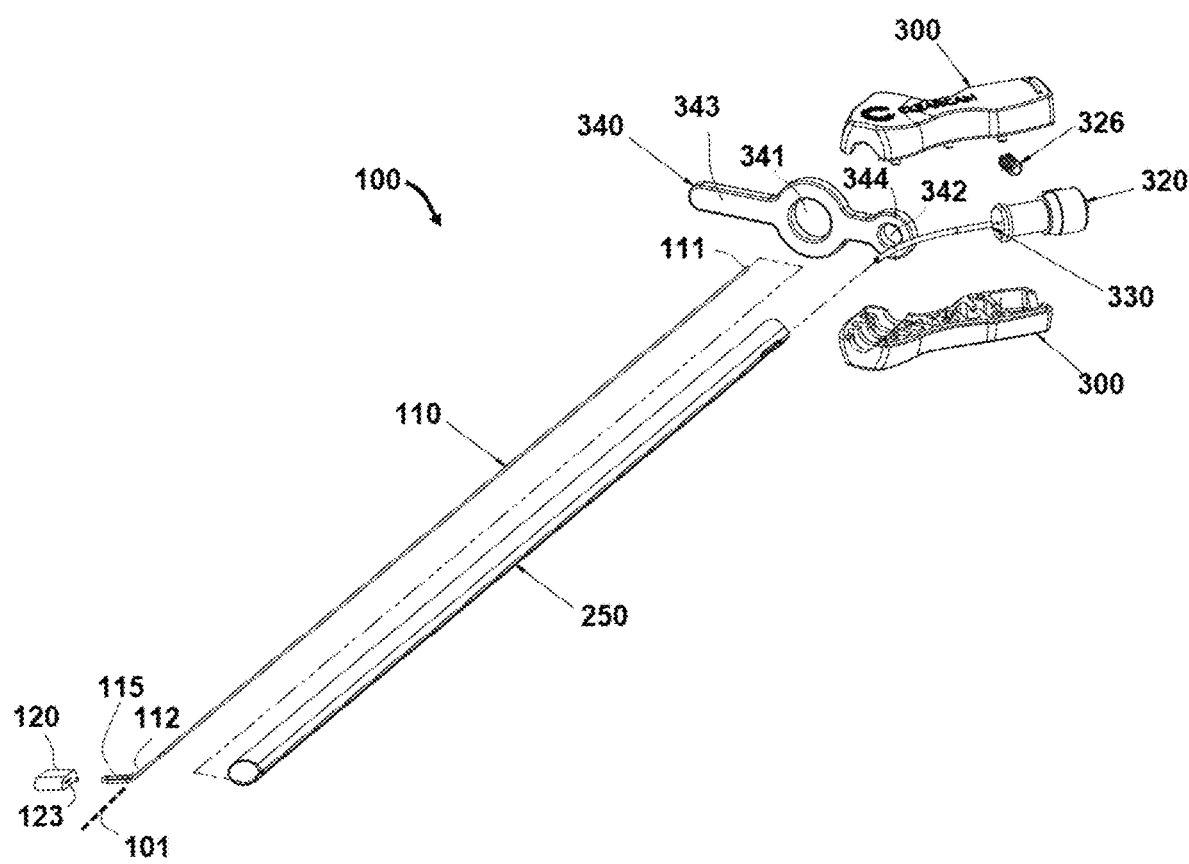
FIG. 6 illustrates an exploded view of the embodiment of FIG. 4

In particular, actuation member 320 can be rotated such that rotatable transverse member 120 is aligned with retaining member 250 as shown in FIG. 4. Device 100 and/or elongated instrument 200 can then be moved such that rotatable transverse member 120 is positioned proximal to the distal end of the elongated instrument. For example, the user can pull actuation member 320 in a direction away from handle 300 (and/or push the elongated instrument further into retaining member 250) such that the distance between rotatable transverse member 120 and distal end 251 of retaining member 250 is reduced. Such movement can be continued until rotatable transverse member 120 engages the distal end of the elongated instrument located within retaining member 250.

Actuation member 320 can then be rotated such that rotatable transverse member 120 is rotated via longitudinal wire member 110. The rotation of rotatable transverse member 120 can remove matter (e.g. via a wiping, cleaning or scraping action) from a surface at the distal end of the elongated instrument. In certain embodiments, actuation member 320 is only capable of being rotated one direction (e.g. either clockwise or counter-clockwise) to prevent buildup of debris on both sides of rotatable transverse member 120, and thereby prevent re-distributing debris on the surface of the elongated instrument. In other embodiments, actuation member 320 can be operated to rotate bi-directionally to allow for user-preferred actuation.

In particular embodiments, actuation member 320 can then be moved toward handle 300 (and/or the elongated instrument can be withdrawn slightly from retaining member 250) such that rotatable transverse member 120 is moved laterally away from retaining member 250 and the elongated instrument. Actuation member 320 can also be rotated to position rotatable transverse member 120 such that rotatable transverse member 120 does not interfere with operation of the elongated instrument (e.g. rotatable transverse member 120 is not aligned with retaining member 250 and does not block the view of a laparoscope inserted in retaining member 250). Accordingly, the elongated instrument can perform its desired function without interference from rotatable transverse member 120.

In exemplary embodiments, rotatable transverse member 120 may be a soft, flexible material that can remove matter from a distal end of an elongated instrument (e.g. a lens of a laparoscope or other viewing instrument) without damaging the distal end of the instrument. For example, in specific embodiments rotatable transverse member 120 may be formed from or comprise a rubber, elastomer, foam, sponge, thermoplastic polyurethane (TPU), thermoplastic elastomers (TPE), medical-grade silicone, silk, polyester, microfiber, or napped material to engage the surface to be cleaned on the elongated instrument. In certain embodiments, materials such as thermoplastic polyurethane (TPU), thermoplastic elastomers (TPE) and medical-grade silicone can be overmolded or insert molded.

It is understood that features and aspects of the embodiment shown in FIGS. 1-3 and 4-13 can be combined with features and aspects of other embodiments shown herein and/or modified. For example, the embodiment shown in FIGS. 4-13 could be modified such that actuation member 320 provided rotational movement only and did not provide lateral translation of longitudinal wire member 110. In such embodiments, lateral movement between the distal end of the elongated instrument and rotatable transverse member could be accomplished by moving the elongated instrument laterally within retaining member 250 or moving the entire device 100 laterally with respect to the port of entry into the cavity.

In addition, certain embodiments may provide for vacuum, liquid or surfactant delivery. Such provisions could go to or from the surface of the elongated instrument, or to or from the rotatable transverse member. In certain embodiments, the rotatable transverse member could be coated in cleaning liquid, or absorb it for future distribution to scope upon contact. In certain embodiments, the surface of the elongated instrument or the rotatable transverse member could also be coated in material that prevents buildup of debris (dust, blood, oils, fats, etc.)

Particular embodiments may also provide for passive defogging of the surface of the elongated instrument that is cleaned via built in "natural" humidity collection. For example, the geometry and size of the retaining member can be selected to allow for collection of vapor on the retaining member walls when environmental conditions are favorable. When the elongated instrument is inserted through the retaining member, vapor droplets adhering to walls may contact the elongated instrument surface, thereby passively distributing the droplets onto the instrument surface. This can further create a thin film or layer of the collected liquid (which could be a warm or cold liquid) onto the instrument surface. In function, the liquid is transparent, which can maintain clear visibility through the instrument surface when the surface is a lens. In addition, the film or thin layer of liquid prevents fog buildup, as the surface does not collect additional condensation on top of the thin layer of condensation that was just collected during the insertion of the instrument into the cavity. The process may be a result of the open-nature of the tubular retaining member that allows for the movement of cool air into the warm cavity (i.e. temperature difference) to interact with the warm moist environment, which meets temperature and humidity conditions needed for vapor droplets to form on inner wall of the tubular retaining member.

Particular embodiments may also comprise an actuation mechanism for a robot in which the actuation member or members are combined with a docking station that are able to integrate with a robot. In certain embodiments, power can come via robot electrically, or can be transferred via docking station where the device itself does not take in electrical power, but docks in a manner able to accept mechanical energy. For example, the electric robot turns gears, the device docks, and gears on robot turn gears on device. Other embodiments could work with cables or other mechanisms to mechanically transfer energy, or could utilize a separate actuation station not powered by the robot that draws power elsewhere, e.g. a battery or electrical outlet.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 5,392,766
U.S. Pat. No. 5,658,273
U.S. Pat. No. 6,354,992
U.S. Pat. No. 8,001,984
U.S. Pat. No. 8,047,215
U.S. Pat. No. 8,535,220
U.S. Pat. No. 8,690,764
US 20020065450
US 20060293559
US 20100139018
US 20120101338
US 20140171739
CA 2400381
CN 102578999
CN 203917219
CN 202892095
IEEE Transactions on Industry Applications; IA-15(6):681-687; December 1979; "A theoretical Study of the Mechanics of a Zerographic Cleaning Blade", Ganesh L. Harpavat.

The invention claimed is:

1. A laparoscope cleaning apparatus, comprising:
a retaining member adapted for having a laparoscope mounted thereon;
a handle attached to a proximate end portion of the retaining member;
a cleaning member adjacent to a distal end portion of the retaining member;
an actuation member translatably and rotatably engaged with the handle to enable independent axial translation movement and rotational movement of the actuation member, wherein the actuation member is coupled to the cleaning member to enable rotation of the actuation member to provide corresponding rotational movement of the cleaning member and axial translation of the actuation member to provide corresponding axial translation movement of the cleaning member, and wherein a longitudinal axis of the actuation member is skewed with respect to a longitudinal axis of a central aperture of the retaining member;
a longitudinal wire member having the cleaning member attached thereto at a distal end portion thereof and having the actuation member attached thereto at a proximate end portion thereof; and
a guide member attached to the handle, wherein an aperture extends within the guide member along a length thereof, wherein the longitudinal wire member extends through the aperture, wherein the guide member comprises a curved portion and wherein the guide member is positioned within the handle to cause a tangential axis extending through a first end of the curved portion extends approximately parallel with the longitudinal axis of the central aperture of the retaining member and to cause a tangential axis extending through a second end of the curve portion extends approximately colinear with the longitudinal axis of the actuation member, wherein:
the retaining member comprises a relief extending along at least a portion of a length of the retaining member;
a longitudinal axis of the relief extends approximately parallel to the longitudinal axis of the central aperture of the retaining member;
at least a portion of the longitudinal wire member between said distal and proximate end portions thereof is within the relief;
the retaining member comprises a slot therein at the proximate end portion thereof;
the slot intersects the relief; and
the first end of the curved portion of the guide member is at least partially within the slot.

2. The laparoscope cleaning apparatus of claim 1 wherein a longitudinal axis of the actuation member is an axis of rotation for said rotation of the actuation member and an axis of translation for said translation of the actuation member.

3. The laparoscope cleaning apparatus of claim 1 wherein:
the retaining member comprises a relief extending along at least a portion of a length of the retaining member; and
at least a portion of the longitudinal wire member between said distal and proximate end portions thereof is within the relief.

4. The laparoscope cleaning apparatus of claim 3 wherein at least a portion of the relief intersects the central aperture of the retaining member.

5. The laparoscope cleaning apparatus of claim 1 wherein at least a portion of the relief intersects the central aperture of the retaining member.

6. A laparoscope cleaning apparatus, comprising:
a tubular member adapted for having a laparoscope engaged therewith, wherein the tubular member comprises a relief extending along at least a portion of a length of the tubular member and wherein a longitudinal axis of the relief extends approximately parallel to a longitudinal axis of the central aperture of the tubular member;
a longitudinal wire member having a distal end portion and a proximate end portion, wherein at least a portion of the longitudinal wire member between said distal and proximate end portions thereof is within the relief;
a cleaning member located adjacent to a distal end portion of the tubular member, wherein the cleaning member is attached the distal end portion of the longitudinal wire member;
a handle attached to a proximate end portion of the tubular member;
an actuation member translatably and rotatably engaged with the handle to enable independent axial translation movement and rotational movement of the actuation member, wherein the actuation member is attached to the proximate end portion of the longitudinal wire member to enable rotation of the actuation member to provide corresponding rotational movement of the cleaning member and axial translation of the actuation member to provide corresponding axial translation movement of the cleaning member, wherein the longitudinal wire member extends contiguously from the cleaning member to the actuation member and wherein a longitudinal axis of the actuation member is skewed with respect to the longitudinal axis of the central aperture of the tubular member; and
a guide member attached to the handle, wherein an aperture extends within the guide member along a length thereof, wherein the longitudinal wire member extends through the aperture, wherein the guide member comprises a curved portion and wherein the guide member is positioned within the handle to cause a tangential axis extending through a first end of the curved portion extends approximately colinear with the longitudinal axis of the relief and to cause a tangential axis extending through a second end of the curve portion extends approximately colinear with the longitudinal axis of the actuation member, wherein:
the tubular member comprises a slot therein at the proximate end portion thereof;
the slot intersects the relief; and
the first end of the curved portion of the guide member is at least partially within the slot.

7. The laparoscope cleaning apparatus of claim 6 wherein at least a portion of the relief intersects the central aperture of the tubular member.

8. The laparoscope cleaning apparatus of claim 6 wherein the longitudinal axis of the actuation member is an axis of rotation for said rotation of the actuation member and an axis of translation for said translation of the actuation member.

9. The laparoscope cleaning apparatus of claim 1 wherein at least a portion of the relief intersects the central aperture of the tubular member.

* * * * *